(12) United States Patent
Boon et al.

(10) Patent No.: US 6,427,085 B1
(45) Date of Patent: Jul. 30, 2002

(54) CARDIAC SENSE AMPLIFIER FOR CAPTURE VERIFICATION

(75) Inventors: Scot C. Boon, Lino Lakes; Mark Gryzwa, Woodbury; Michael Lyden, Shoreview; Qingsheng Zhu, Little Canada; Paul Haefner, Circle Pines, all of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/309,951

(22) Filed: May 11, 1999

(51) Int. Cl.[7] .................................................. A61N 1/37
(52) U.S. Cl. ........................................................ 607/28
(58) Field of Search ................................. 600/508–522; 607/28, 9

(56) References Cited

U.S. PATENT DOCUMENTS

| | | | |
|---|---|---|---|
| 5,161,529 A | 11/1992 | Stotts et al. ................ 128/419 |
| 5,222,493 A | 6/1993 | Sholder ....................... 128/419 |
| 5,324,310 A | 6/1994 | Greeninger et al. .......... 607/28 |
| 5,350,410 A | 9/1994 | Kleks et al. .................. 607/28 |
| 5,683,431 A | 11/1997 | Wang ........................... 607/28 |
| 5,871,512 A | 2/1999 | Hemming et al. ............ 607/28 |
| 6,112,119 A | * 8/2000 | Schuelke et al. |

* cited by examiner

*Primary Examiner*—Mark Bockelman
(74) *Attorney, Agent, or Firm*—Nikolai & Mersereau, P.A.

(57) ABSTRACT

A cardiac rhythm management device having a capture verification sensing circuit for use in either a normal beat to beat pacing mode or an autothreshold mode. The cardiac rhythm management device is coupled to one or more pacing leads having pacing/sensing electrodes coupled thereto, and includes a sensing circuit for sensing electrical activity of the patient's heart, wherein the sensing circuit includes a dedicated evoked response sense amplifier and at least one high pass coupling capacitor electrically connected as a portion of a high pass network and between a pacing/sensing electrode and a blanking switch. A plurality of high pass coupling capacitors are coupled in parallel each having a separate blanking switch, thereby creating a differential network to offset imbalance sensed from the electrode due to extraneous factors.

5 Claims, 7 Drawing Sheets

CARDIAC SENSE AMPLIFIER FOR CAPTURE VERIFICATION

BACKGROUND OF THE INVENTION

I. Field of the Invention

The present invention relates generally to the field of cardiac rhythm management devices, including atrial, ventricular, and dual chamber pacemakers. More specifically, the present invention relates to a portion of the sensing circuit utilized during capture verification. The sense amplifier of the present invention includes a dedicated wide-band pass filter and reduces both the amplitude of the pacing artifact and the required recovery time, without requiring unipolar sensing or low impedance leads. The cardiac rhythm management device utilizes an adaptive evoked response sensing threshold and may operate in a normal beat to beat pacing mode and/or an autothreshold mode.

II. Discussion of the Prior Art

For the most part, prior art implantable cardiac rhythm management devices, including bradycardia and tachycardia pacemakers and cardiac defibrillators, have sense amplifier circuits for amplifying and filtering electrogram signals sensed through electrodes placed in or on the heart and which are coupled by suitable leads to the implantable cardiac rhythm management device. The signals emanating from the sense amplifier are applied to one input of a comparator circuit whose other input is connected to a reference potential. Only when an electrogram signal from the sense amplifier exceeds the reference potential threshold will it be treated as a cardiac paced or sensed beat. The source reference potential may be referred to as a sensing threshold. Only when an electrogram signal from the sense amplifier exceeds the preprogrammed reference potential threshold will it be treated as a cardiac paced or sensed beat. The source referenced potential may be referred to as an evoked response detection threshold.

For cardiac pacer systems having beat-to-beat capture verification and backup pacing it is necessary to detect the evoked response during the QRS complex. Pacing artifacts and the required recovery response period make it difficult to detect capture during the interval coinciding with the QRS complex. Thus, there is a need for a sense amplifier that assists in the reduction of pacing artifact and required recovery response period.

Typically, the reference potential threshold is set at a fixed amount that is expected to exceed the maximum amplitude of artifact. If, however, the threshold is not set high enough, then artifact may result in false capture declaration. Further, if the reference potential threshold is set too high, then the amplitude associated with an R-wave may not be sufficient to trigger the reference potential threshold.

Several factors influence the amplitude associated with R-waves. For example, respiration of the patient fluctuates the amplitude of the evoked response in a cyclic fashion increasing and decreasing over several beats. This fluctuation makes it even less desirable for the reference potential threshold to be set at a fixed amount. Other factors, described in greater detail below, affect the amplitude of the evoked response. Thus, a need exists for a cardiac rhythm management device that automatically adjusts the evoked response detection threshold in conjunction with fluctuations in the amplitude associated with a particular R-wave, taking into account the modulation of the amplitude corresponding to the evoked response for each R-wave.

U.S. Pat. No. 5,161,529 issued to Stotts et al. (the '529 patent) describes a sense amplifier having a switched capacitor circuit, wherein the amplifier's bandpass frequency characteristics are switched during a cardiac cycle to selectively vary the cardiac signal frequencies subject to sensing. In this manner Stotts et al. describes switching the bandpass frequency of the sense amplifier to a high bandpass frequency to detect intrinsic cardiac response and, within a suitable delay interval (10–30 ms) from delivery of a pacing stimulus, to a low bandpass frequency to detect an evoked response. Although Stotts et al. further describes optionally increasing the delay interval to an even higher bandpass frequency to assure rapid attenuation of any pacing artifact, the suitable delay interval was identified as ranging between 10–30 ms. Thus, there is a need for a sense amplifier that reduces both the amplitude of the pacing artifact and the required recovery time.

The success of a cardiac rhythm management device in causing a depolarization or evoking a response hinges on whether the energy of the pacing stimulus as delivered to the myocardium exceeds a threshold value. This threshold value, referred to as the capture threshold, represents the amount of electrical energy required to alter the permeability of the myocardial cells to thereby initiate cell depolarization. If the energy of the pacing stimulus does not exceed the capture threshold, then the permeability of the myocardial cells will not be altered and thus no depolarization will result. If, on the other hand, the energy of the pacing stimulus exceeds the capture threshold, then the permeability of the myocardial cells will be altered such that depolarization will result.

Changes in the capture threshold may be detected by monitoring the efficacy of stimulating pulses at a given energy level. If capture does not occur at a particular stimulation energy level which previously was adequate to effect capture, then it can be surmised that the capture threshold has increased and that the stimulation energy should be increased. On the other hand, if capture occurs consistently at a particular stimulation energy level over a relatively large number of successive stimulation cycles, then it is possible that the capture threshold has decreased such that the stimulation energy is being delivered at a level higher than necessary to effect capture. This can be verified by lowering the stimulation energy level and monitoring for loss of capture at the new energy level.

The ability to detect capture in a cardiac rhythm management device is extremely desirable in that delivering stimulation pulses having energy far in excess of the patient's capture threshold is wasteful of the cardiac rhythm management device's limited power supply. In order to minimize current drain on the power supply, it is desirable to automatically adjust the cardiac rhythm management device such that the amount of stimulation energy delivered to the myocardium is maintained at the lowest level that will reliably capture the heart. To accomplish this, a process known as "capture verification" must be performed wherein the cardiac rhythm management device monitors to determine whether an evoked response or R-wave occurs in the heart following the delivery of each pacing stimulus pulse.

For the most part, prior art implantable cardiac rhythm management devices, including bradycardia and tachycardia pacemakers and cardiac defibrillators, have sense amplifier circuits for amplifying and filtering electrogram signals sensed through electrodes placed in or on the heart and which are coupled by suitable leads to the implantable cardiac rhythm management device. The signals emanating from the sense amplifier are applied to one input of a comparator circuit whose other input is connected to a reference potential. Only when an electrogram signal from the sense amplifier exceeds the reference potential threshold will it be treated as an evoked response. The source reference potential may be referred to as a sensing threshold. In some instances the amplitude of pacing artifact may be so great that it becomes difficult to distinguish the amplitude corresponding to an evoked response with the amplitude corresponding to artifact. Hence, there is a need for a capture verification circuit of a cardiac rhythm management device capable of differentiating between the amplitude corresponding to evoked response and the amplitude corresponding to artifact of a sensed signal. There is a further need for a capture verification circuit suitable for use with either unipolar or bipolar stimulation and which does not depend upon lead placement. The present invention meets these and other needs that will become apparent from a review of the description of the present invention.

SUMMARY OF THE INVENTION

It is accordingly the objective of the present invention to provide for a cardiac rhythm management device having a capture verification sensing circuit which reduces both the amplitude of the pacing artifact and the required recovery time, without requiring unipolar sensing or low impedance leads. The cardiac rhythm management device of the present invention may operate in a normal beat to beat stimulation mode and/or an autothreshold mode and may be electrically coupled to one or more known suitable leads having pacing/sensing electrodes coupled thereto. The electrodes of each lead are selectively positioned within the heart and are coupled to an electrical conducting means for electrically coupling the electrodes to the cardiac pacer. Without any limitation intended, the electrical conductors and/or electrical conducting means as identified herein may comprise a circuitry having a plurality of electrical conducting segments of known suitable construction.

The cardiac rhythm management device has means for both selectively delivering electrical stimuli to a patient's heart and for detecting at least one of intrinsic and paced stimulations. For ease of discussion and without any limitation intended the sensing circuit of the present invention will be described incorporated into a cardiac pacer. The cardiac pacer includes a sensing amplifier electrically coupled to the electrodes, wherein the sense amplifier amplifies and filters electrocardiogram signals collected by the electrodes. A dedicated evoked response sense amplifier is included having a wide-band pass filter. Also included is a power supply, controller coupled to receive the sensed electrogram signals and means controlled by the controller for applying cardiac stimulation pulses to a patient's heart, wherein the stimulation pulses are applied in response to control signals from the controller.

The controller may be in any of several forms including a dedicated state device or a microprocessor with code, and may include ROM memory for storing programs to be executed by the controller and RAM memory for storing operands used in carrying out the computations by the controller. Those skilled in the art will appreciate that pacing circuitry, sensing circuitry, timing circuitry, and wave detection circuitry among others may all be included within the controller. The controller and components contained therein or coupled thereto detect and distinguish cardiac depolarization deflections and noise deflections from the electrocardiogram signal. A peak detector, for example, may be utilized to determine the amplitudes of the cardiac depolarization deflections and noise deflections. The sense amplifier of the present invention may be utilized during a capture verification mode of the cardiac pacer to reduce both the amplitude of the pacing artifact and the required recovery time of the pacing/sensing circuit.

The sense amplifier is formed as a part of the sensing circuit and includes the following components electrically coupled together via an electrical conductor: a preamplifier, a first high pass coupling capacitor, and a blanking switch. The high pass coupling capacitor is electrically coupled between the electrodes and the pre-amplifier. Further, the blanking switch is electrically coupled between the high pass coupling capacitor and the pre-amplifier. Electrically coupling the high pass coupling capacitor between the electrodes and the blanking switch reduces the affects of polarization voltages or afterpotentials. Additionally, a high pass termination resistor may be coupled to the electrical conductor between the blanking switch and the pre-amplifier.

Also, a low pass coupling capacitor and low pass resistor may be connected to the electrical conductor between the blanking switch and the pre-amplifier, wherein a low pass bi-pass switch may be connected to the electrical conducting means between the blanking switch and the pre-amplifier to selectively connect the low pass coupling capacitor and the low pass resistor to the electrical conductor. Further, an input blanking means may be connected to the electrical conductor between the blanking switch and the pre-amplifier for selectively blanking sensed electrical activity. Those skilled in the art will appreciate that a second sensing means for sensing electrical activity of the patient's heart may be connected in parallel with the first sensing means as described above, thereby creating a differential network to offset imbalance sensed from the electrode due to extraneous factors.

OBJECTS

It is accordingly a principal object of the present invention to provide a capture verification sensing circuit suitable for use in unipolar or bipolar sensing, wherein the leads may have a wide range of impedances.

Another object of the present invention is to provide a cardiac pacer that shortens the pacing afterpotentials and reduces sensing circuit reaction to residual charges.

A further object of the present invention is to provide a cardiac pacer having a capture verification sensing circuit which reduces both the amplitude of the pacing artifact and the required recovery time, without requiring unipolar sensing or low impedance leads.

These and other objects and advantages of the present invention will be readily apparent to those skilled in the art from a review of the following detailed description of the preferred embodiment in conjunction with the accompanying claims and drawings in which like numerals in the several views refer to corresponding parts.

DESCRIPTION OF THE PREFERRED EMBODIMENT

Figure 1:
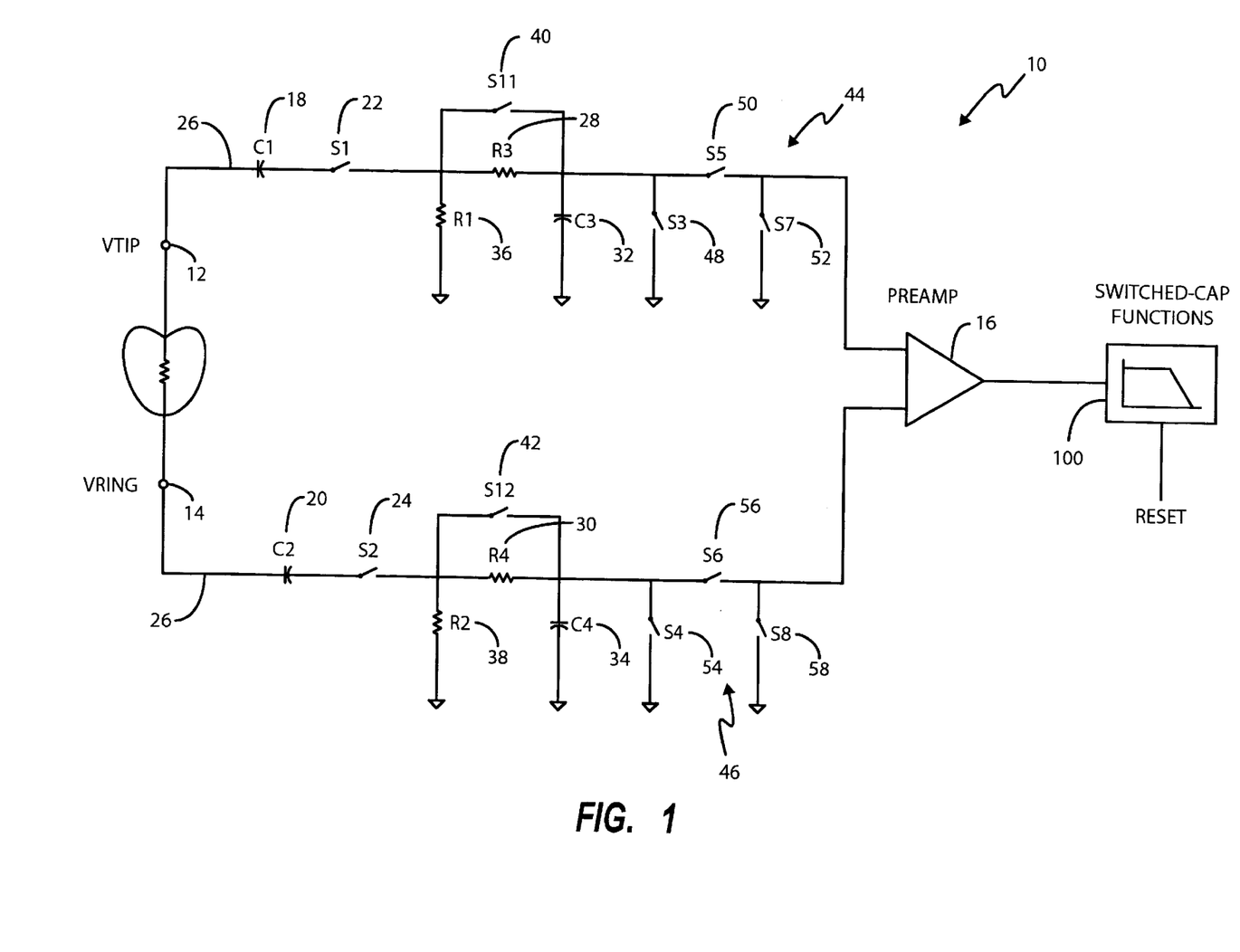
FIG. 1 is a schematic diagram of a portion of the sense amplifier of the present invention.

Referring first to FIG. 1, the portion of the sense amplifier 10 of the present invention is generally shown having a differential network which offsets imbalances sensed from the electrodes 12 and 14 due to extraneous factors. The differential network sense amplifier 10 generally includes a preamplifier 16, first and second high pass coupling capacitors 18 and 20, and first and second blanking switches 22 and 24 electrically connected together via a plurality of electrical conducting means 26 segments of known suitable construction. The first and second high pass coupling capacitors 18 and 20 are electrically coupled between the electrodes, 12 and 14 respectively, and the pre-amplifier 16. Further, the first and second blanking switches 22 and 24 are electrically coupled between the first and second high pass coupling capacitors, 18 and 20 respectively, and the pre-amplifier 16. Electrically coupling the high pass coupling capacitors 18 and 20 between the electrodes 12 and 14 and the blanking switches 22 and 24 reduces the affects of polarization voltages or afterpotentials. Although the sense amplifier having a differential network will be described below, those skilled in the art will appreciate that a single network having a first high pass coupling capacitor 18 electrically connected between the electrode 12 and the first blanking switch 22 reduces pacing artifact and response time of the sensing circuit. High pass termination resistors 28 and 30 may be connected to the circuit with electrical conductor segments 26 between the blanking switches 22 and 24 respectively and the pre-amplifier 16.

Low pass coupling capacitors 32 and 34 and low pass resistors 36 and 38 may be connected via electrical conductor 26 between the blanking switches 22 and 24 respectively and the pre-amplifier 16, wherein low pass bi-pass switches 40 and 42 may be connected via the electrical conducting means segments 26 between the blanking switches 22 and 24 respectively and the pre-amplifier 16 to selectively connect the low pass coupling capacitors 32 and 34 respectively and the low pass resistors 36 and 38 to the electrical circuit. Further, an input blanking means 44 and 46 including without limitations switches 48, 50, 52 and 54, 56, 58 respectively, may be connected to the electrical conductor 26 between blanking switch 22 and 24 respectively and the pre-amplifier 16 for selectively blanking sensed electrical activity.

Without any limitation intended the first and second high pass coupling capacitors 18 and 20 may have a capacitance of a suitable range with a capacitance of 0.1 microfarads being preferred, the low pass coupling capacitors 32 and 34 may have a capacitance of a suitable range with 3600 picofarads being preferred, and the high and low pass resistors 28, 30, 36, 38, may have a resistance of a suitable range with a resistance of 200 k ohms being preferred.

Figure 2:
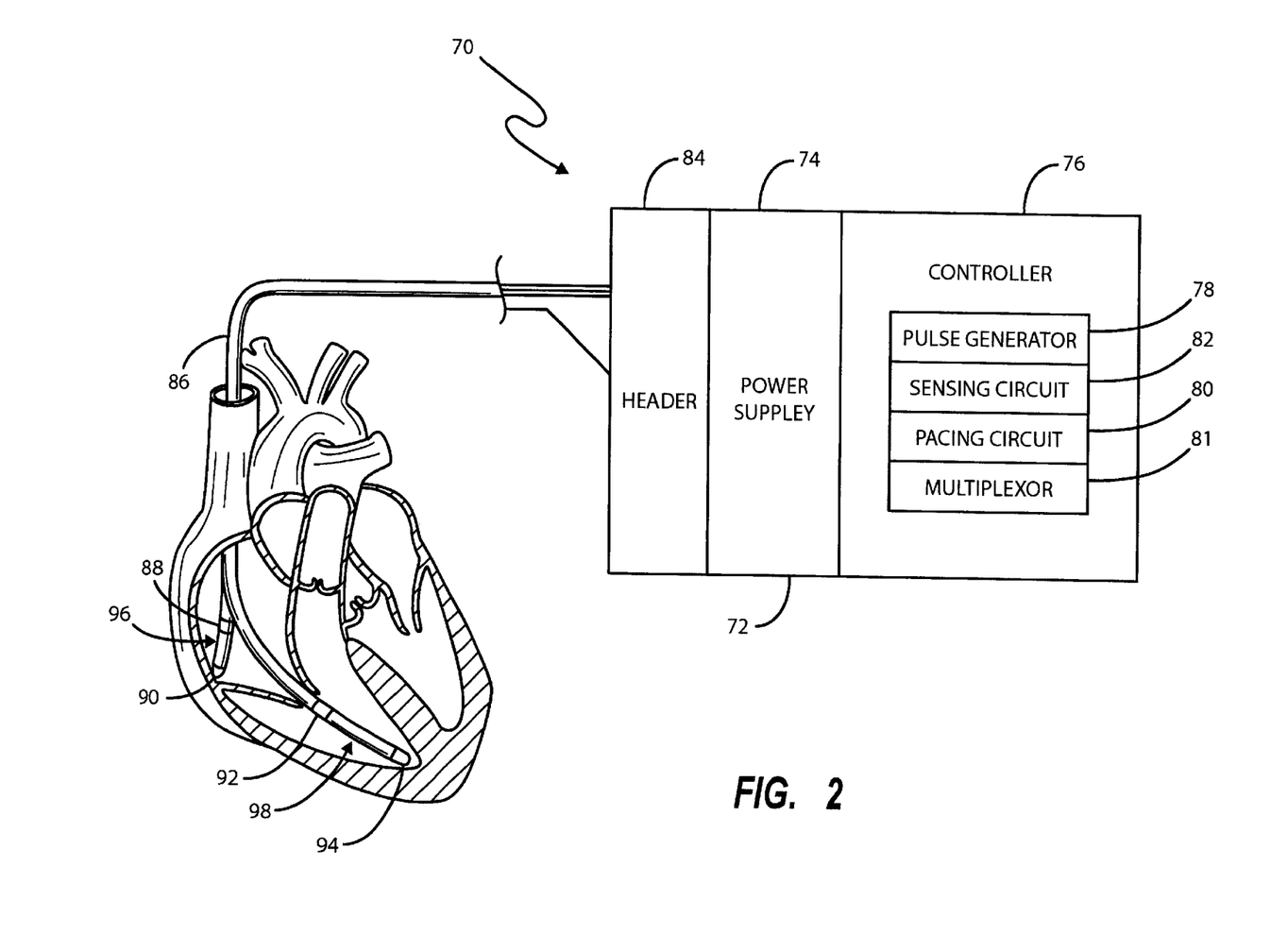
FIG. 2 is a partial sectional fragmentary block diagram depicting a cardiac rhythm management device incorporating the improved sense amplifier for automatic capture detection in accordance with the present invention.

Referring now to FIG. 2, the present invention may find application in a variety of implantable or external cardiac rhythm management devices. For purposes of illustration and ease of discussion, the present invention will be described in connection with an implantable rate adaptive cardiac pacer 70 having an external housing or can 72, wherein a power supply 74 and controller 76 are contained therein. As described above, the controller may be in any of several forms including a dedicated state device or a microprocessor with code, and may include ROM memory for storing programs to be executed by the controller and RAM memory for storing operands used in carrying out the computations by the controller. The controller 76 may include a pulse generator 78 and pacing circuit 80 for selectively delivering electrical stimuli to a patient's heart and a sensing circuit 82 for detecting at least one of intrinsic and paced stimulations of the patients heart. As described in greater detail below, the sensing circuit 82 may include a dedicated evoked response sense amplifier, with multiplexer 81 coupled thereto in a known suitable fashion, wherein the evoked response sense amplifier may be utilized in either atrial or ventricular sensing. One or more leads of known suitable construction may be electrically connected to the cardiac pacer 70 through a header 84. The split lead 86 illustrated in FIG. 2 includes electrodes 88 and 90 positioned in the right atrium 96 for pacing and sensing therein, and electrodes 92 and 94 positioned in the right ventricle 98 for pacing and sensing therein. The electrodes 88–94 are electrically coupled to the cardiac pacer 70 in a known suitable fashion.

In use, immediately after delivering a pacing stimulus to the patient's heart, the controller 76 initiates a blanking period for the sensing amplifier 10. In the preferred embodiment, a dedicated evoked response channel and a dedicated intrinsic response channel interconnect with the sense amplifier 10. With reference to FIG. 2, during and immediately after the pacing stimulus is delivered to the lead 86, lead blanking switches 22 and 24 and input blanking switches 50 and 56 are open, thereby preventing any charge of capacitors 18 and 20 and disconnecting the capacitors 32 and 34 and resistors 28 and 30 from the preamplifier input. The voltages on the C1/S1 (18/22) and C2/S2 (20/24) nodes follows the electrodes during pace and recharge. During this same period, switches 40, 42, 48, 54, 52, and 58 are closed, thereby grounding capacitors 32 and 34 and resistors 28 and 30.

The controller 76 controls period of time that switches 22, 24, 50 and 56 are open or closed. The pace blanking signal from the controller 76 is synchronized with switched capacitor clocks of the switched capacitor functions 100 to minimize the introduction of transients into the switched capacitor circuits. Further, the controller 76 disables sampling during the blanking period and switched capacitor filters are zeroed or reset. The dedicated channels of the switched capacitor functions 100 is switched to span lower frequencies while sensing evoked response (ER) and is switched to span higher frequencies for intrinsic response (IR). This switching is synchronized to the switched capacitor clocks to minimize transients. The frequency response is also switched dependant upon whether sensing is unipolar or bipolar sensing, since unipolar evoked response has a lower frequency. Those skilled in the art will further appreciate that when implementing the sensing circuit of the present invention a different mid-band gain may be set for evoked response and intrinsic response.

In the preferred embodiment switches 22, 24, 50 and 56 are open for approximately 8–15 milliseconds beginning prior to delivery of the pacing stimulus. Once the predetermined blanking period has ended, switches 22, 24, 50 and 56 are closed and switches 40, 42, 48, 54, 52, and 58 are open. In this manner the high pass coupling capacitors 18 and 20, positioned within the high pass network, reduces the amplitude of the pacing artifact. Closing switches 22 and 24 prior to opening switches 40, 42, 48, and 54 eliminates any DC offset remaining across switch 22.

Figure 3:
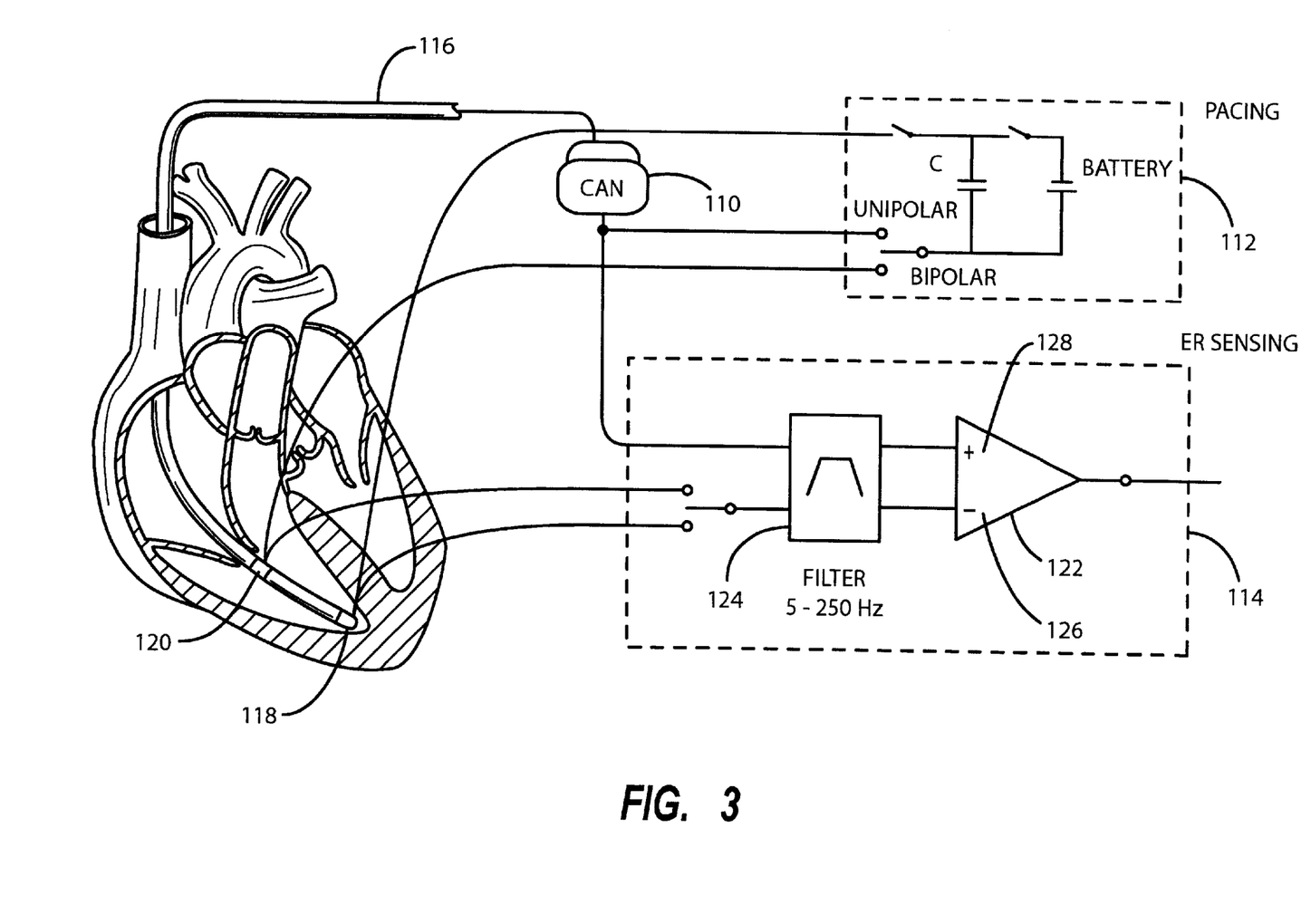
FIG. 3 is a partial sectional view of a lead positioned within the ventricle of a heart and shown electrically coupled to pacing and sensing circuits, wherein the pacing and evoked response sensing circuits are shown partially in block form and exploded from the housing or can of the cardiac rhythm management device.

Referring next to FIG. 3, as described above, the present invention is described in connection with an implantable cardiac pacer having an external housing or can 110, wherein a power supply and controller are contained therein. The pacer includes a pacing circuit and evoked response sensing circuit, a portion of each of which is shown enclosed by blocks 112 and 114 respectively. As described above, the controller may be in any of several forms including a dedicated state device or a microprocessor with code, and may include ROM memory for storing programs to be executed by the controller and RAM memory for storing operands used in carrying out the computations by the controller. The controller may include a pulse generator and pacing circuit 112 for selectively delivering electrical stimuli to a patient's heart and an evoked response sensing circuit 114 for detecting paced stimulations of the patients heart. One or more leads of known suitable construction may be electrically connected to the cardiac pacer. The lead 116 includes electrodes 118 and 120 positioned in the right ventricle for pacing and sensing therein. The electrodes 118 and 120 are electrically coupled to the cardiac pacer and the pacing and sensing circuits 112 and 114 contained therein. The evoked response sensing circuit 114 includes a dedicated sense amplifier 122 and single high pass pole band pass filter 124. The negative terminal or pole 126 of the sense amp 122 is connected via a switch to either electrode 118 or 120. The positive terminal or pole 128 of the sense amplifier 122 is electrically coupled to the electrically conductive housing 110 or indifferent electrode of the cardiac rhythm management device. In this manner, the polarity of the amplitude associated with artifact is opposite the polarity of the amplitude associated with evoked response.

Figure 4:
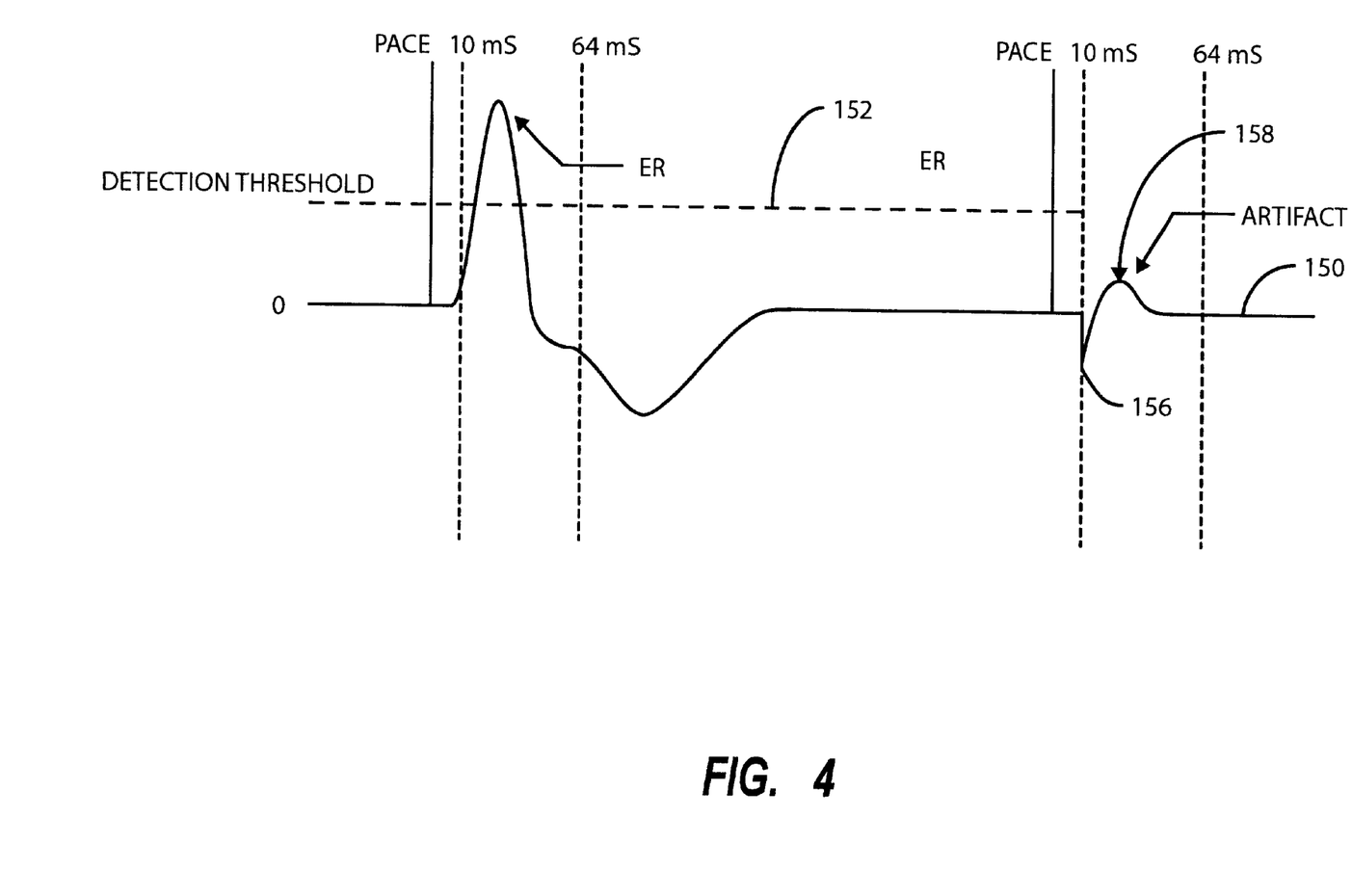
FIG. 4 is a graph of an electrocardiogram signal sensed over time with the sensing circuit of the present invention.

Referring now to FIG. 4, an electrocardiogram signal 150 is shown resulting from a pacing stimulus. Without limitation, the dedicated evoked response sense amplifier is duty cycled and is only turned on by the controller during a predefined capture detection window. The capture detection window shown in FIG. 4 is defined by the time from pacing to 64 msec after pace. Those skilled in the art will appreciate that the capture detection window may be defined either longer or shorter than the period shown in FIG. 4. The evoked response detection threshold is shown by dotted line 152, wherein a positive peak amplitude associated with the evoked response exceeds the evoked response detection threshold. Later in time the artifact associated with recharge is seen having primarily a negative peak amplitude. The minor portion 158 of the signal associated with artifact 156 does not exceed the evoked response detection threshold and does not result in false capture declaration.

Figure 5:
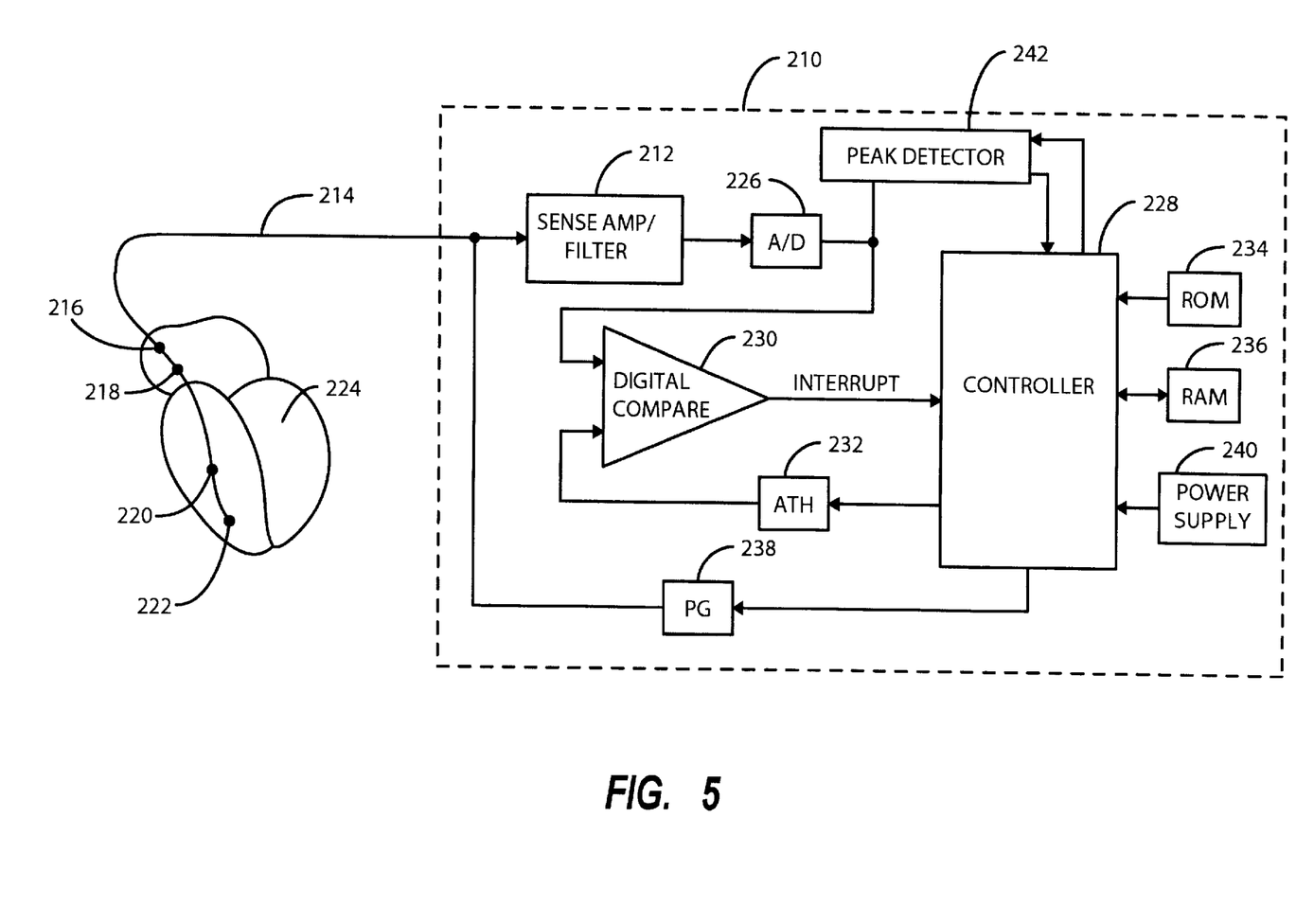
FIG. 5 is a general block diagram of a cardiac rhythm management device that may incorporate the automatic evoked response threshold adjustment of the present invention.

Referring next to FIG. 5, there is illustrated by means of a block diagram, a hardware platform in which the auto-adjust algorithm of the present invention may be utilized. Shown enclosed by the broken line box 210 is circuitry which may be included within a cardiac rhythm management device, such as a pacemaker. It is seen to include a sense amplifier/filter 212 having its input connected by a pacing lead 214. The pacing lead 214 is shown having a plurality of electrodes 216–222 coupled to lead 214 and disposed on or in the heart 224. An electrocardiogram signal is transmitted through the pacing lead 214 to the sense amplifier/filter 212.

In FIG. 5, the lead 214 is shown as a bipolar single pass VDD or DDD lead, various forms of which are known to those skilled in the art. Without limitation, the electrodes 220 and 222 are designed to detect ventricular depolarization while electrodes 216 and 218 sense atrial depolarization. The controller 228 is coupled to power supply 240 and provides a control output to a pulse generator 238 at appropriate times. The resulting pulses are applied over the lead 214 to the electrodes 216, 218, 220 and/or 222 for providing electrical stimulation to the heart 224. The arrangement shown in FIG. 5 can be used for sensing a response evoked by a pacing pulse in the ventricles.

The sense amp/filter circuit 212 conditions the electrogram signal and then applies the conditioned signal to an analog-to-digital converter 226 which converts the conditioned signal to corresponding digital values compatible with a peak detector 242. From the analog-to-digital converter 226, the signal is transmitted to both peak detector 242 and a comparator 230. Without any limitation intended, the peak detector may include a digital comparator and register, wherein the signal transmitted from the A/D converter 226 is continuously compared with an initial value stored in the peak detector register. If the current signal is greater than the value stored in the peak detector, the current value is loaded into the register value and is then stored in the peak detector register as a "maximum" amplitude. The peak detector 242 includes a clearing mechanism controlled by the controller 228. Those skilled in the art will recognize that timers, utilized to activate and deactivate the peak detector, may be either external or internal to the controller 228. Once the peak detector 242 times out, the final peak detector register value is transmitted to the controller 228. In this manner the peak detector 242 may be utilized to determine the amplitudes of the cardiac depolarization events.

The output from the A/D converter 226 may also be applied as a first input to a digital comparator 230. A second reference input is compared by digital comparator to the first input transmitted from the A/D converter 226. The reference input of the comparator 230 is a digital value stored in the ATH register 232. The controller 228 may periodically compute and modify the digital value stored in the ATH register 232. Without limitation, the reference input of the comparator 230 may correspond to, for example, the evoked response detection/sensing A threshold. Of course, other components of suitable known construction are utilized to provide the operable cardiac rhythm management device of the present invention.

The drawing of FIG. 1 shows only one hardware configuration in which the algorithm of the present invention can be implemented. Those skilled in the art will appreciate that the circuit of FIG. 1 can be modified so that, for example, the digital comparator 230 and ATH register 232 can be internal to the controller 228. It is also possible to add an additional digital comparator in parallel with the digital comparator 230 and provide a separate threshold register for corresponding sensing threshold (ST) rather than time sharing the digital comparator 230 between the detection of cardiac depolarization and noise. The controller 228 may be in any of several forms including a dedicated state device or a microprocessor with code, and may include ROM memory 234 for storing programs to be executed by the controller 228 and RAM memory 236 for storing operands used in carrying out the computations by the controller 228.

Figure 6:
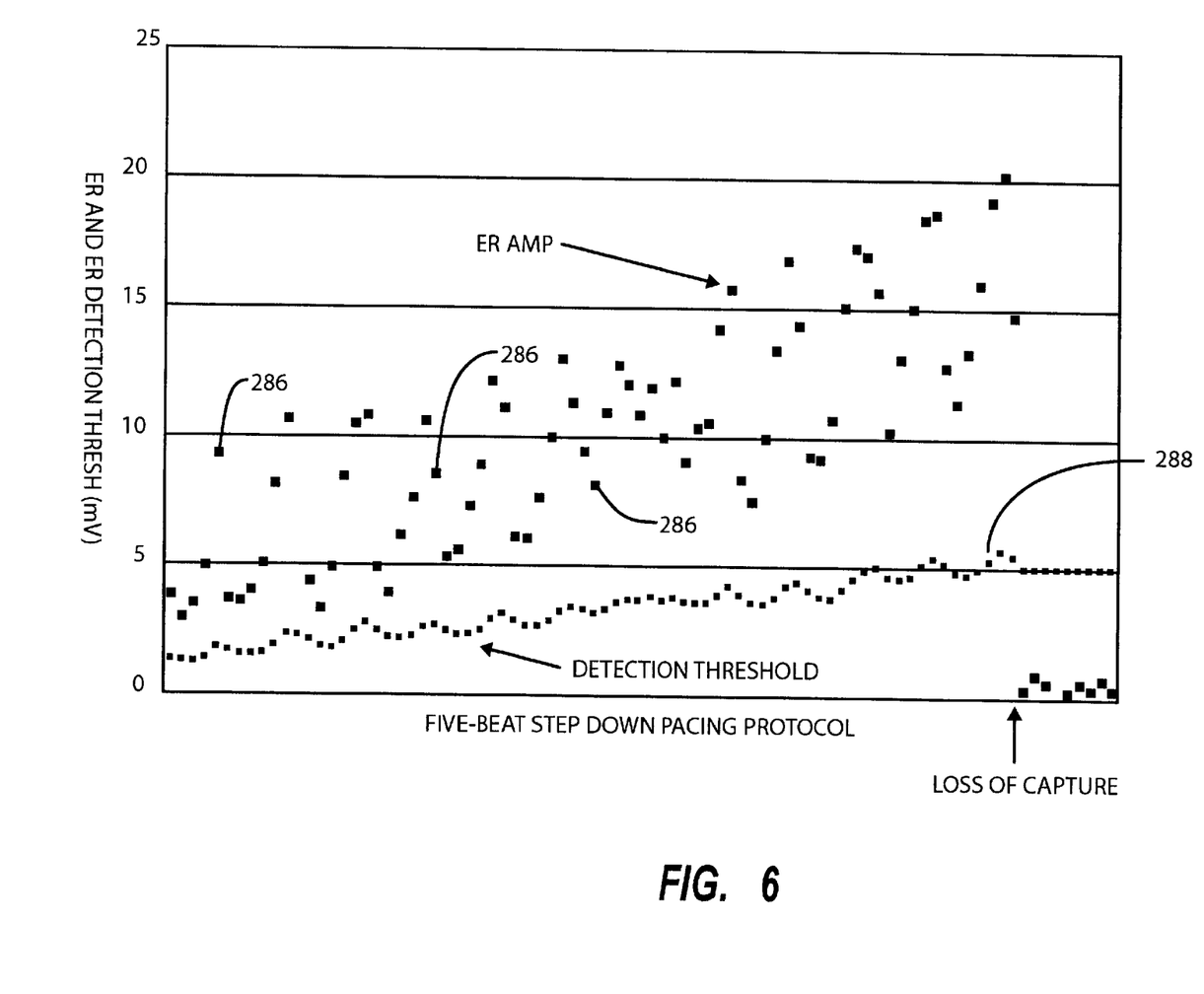
FIG. 6 is a graph of the amplitude of evoked response for several beats during a five-beat step down capture detection pacing protocol.

Referring now to FIG. 6, the maximum amplitude of several R-waves indicated at point 286 are shown measured over time, wherein the "measurements" of the amplitude occurred during a five-beat step down capture detection pacing protocol. The evoked response detection threshold baseline 288 as determined by the method of the present invention is shown, wherein fluctuation in the baseline coincides with the modulation of the evoked response amplitude. In this manner, during beat by beat autocapture, for example, a decrease in the evoked response amplitude is not likely to generate a false negative in capture decision making, thereby eliminating unnecessary backup pacing.

Figure 7:
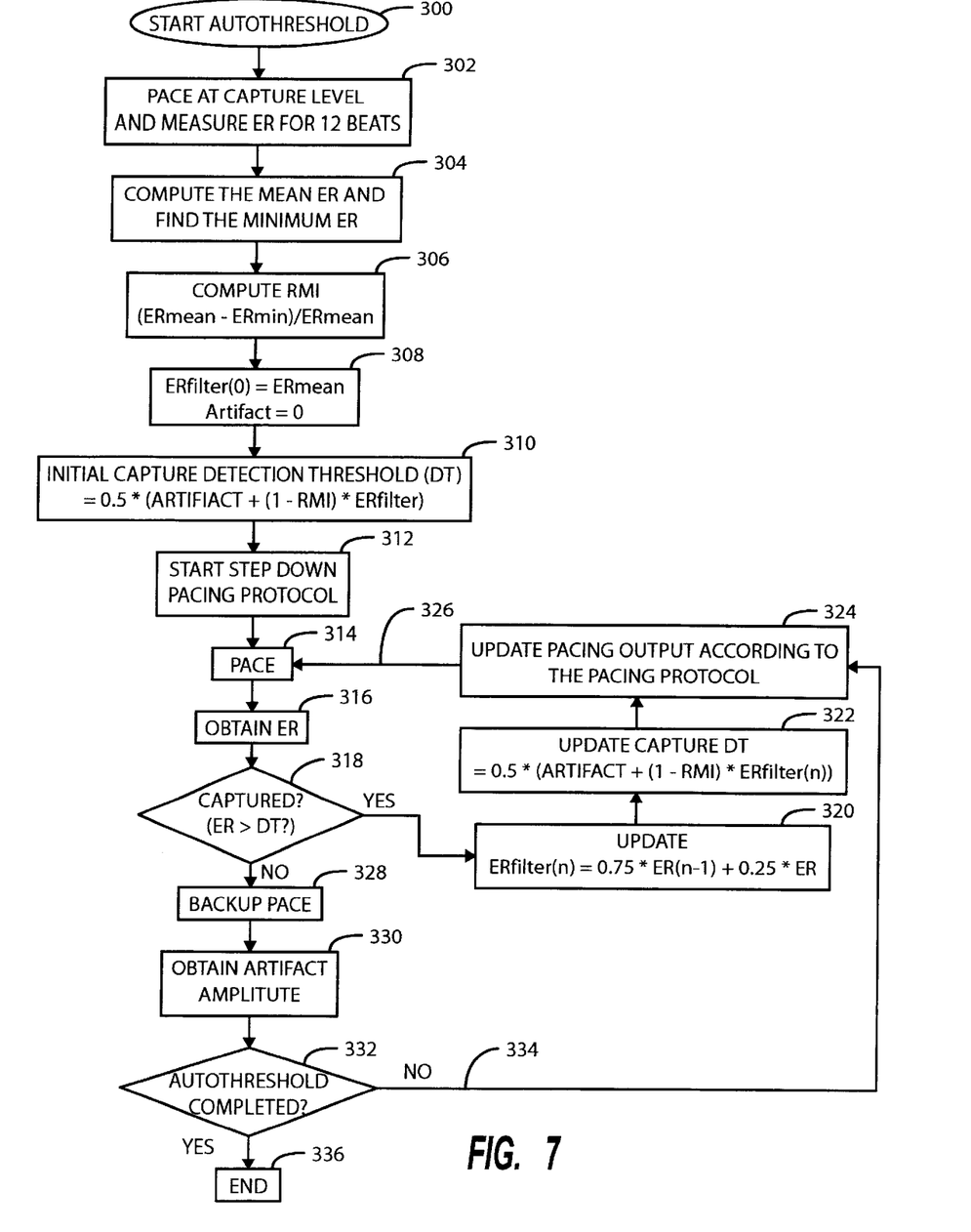
FIG. 7 is a software flow diagram of the automatic adjustment of the evoked response detection threshold algorithm of the present invention.

Without any limitation intended, when an electrocardiogram excursion picked up on lead 214 is signal processed by the sense amplifier/filter circuit 212 and converted to a digital quantity by A/D converter 226, a digital quantity proportional to the excursion is applied to one input of the digital comparator 230 and to the controller 228. If the electrocardiogram excursion exceeds the sensing threshold, the controller processes the signal as a cardiac depolarization, "measuring" the amplitude of the depolarization wave. Once the amplitude measurements have been made for a predetermined number of beats, the controller 228 initiates a sequence to determine and adjust the evoked response detection threshold. FIG. 7 illustrates a method of determining and modulating the evoked response detection threshold in conjunction with the modulating amplitude of evoked response.

Once the automatic evoked response detection threshold determination is initiated (see block 300), the patient's heart is paced at the current capture level for a predetermined number of beats. The maximum amplitude of each evoked response over the predetermined number of beats is measured utilizing the peak detector, comparator and controller as described above in greater detail (see block 302). A value associated with each maximum amplitude may be stored in the memory of the controller. The predetermined number of beats should include at least one complete cycle of the respiration modulation. The mean amplitude and minimum amplitude for all of the maximum amplitudes over the predetermined number of beats is then determined and stored (see block 304). A first constant value referred to as the "Respiration Modulation Index" or RMI is determined according to the following equation:

$$(ER_{mean} - ER_{min})/ER_{mean}$$

wherein $ER_{mean}$ is the mean amplitude for all of the maximum amplitudes over the predetermined number of beats and $ER_{min}$ is the minimum amplitude for all of the maximum amplitudes over the predetermined number of beats (see block 306). A second constant value identified as the $ER_{Filter}$ (described below in greater detail) is initially set equal to the determined $ER_{mean}$ and a value corresponding to an amplitude of artifact is initially set equal to zero (see block 308). The evoked response detection threshold (ERDT) is then determined according to the following equation:

$$ERDT = k(\text{Artifact} + ERM_{min})$$

where k is a predefined constant that may range between 0.1 to 0.9 and $ER_{min}$ is the minimum evoked response due to modulation. The $ER_{min}$ takes into account both the modulation due to respiration and the modulation due to other factors as follows:

$$ER_{min} = (1 - RMI)(ER_{Filter})$$

(see block 310). This evoked response detection threshold (ERDT) may be utilized and updated during a capture detection step down pacing protocol (see block 312). A pacing stimulus is delivered and then the rhythm management device senses for an evoked response (see blocks 314 and 316). A determination is then made whether a signal is sensed having an amplitude greater than the ERDT (see decision block 318).

If a maximum amplitude of the sensed signal exceeds the ERDT it is assumed that this signal corresponds to an R-wave and capture is assumed. The value corresponding to the $ER_{Filter}$ is then updated according to the following equation:

$$ER_{Filter(n)} = a(ER_{Filter(n-1)}) + b(ER_n)$$

where n=0 for the initial determination of the $ER_{Filter}$ value and increases by an integer number for each subsequent determination of the ERDT, and "a" and "b" are coefficients wherein a+b=1 (see block 320). In the preferred embodiment "a" is set equal to 0.75 and "b" is set equal to 0.25. Those skilled in the art will appreciate that the $ER_{Filter}$ provides a moving average of the evoked response, thereby adapting the evoked response detection threshold to changes in the evoked response amplitude. The ERDT is updated according to the following equation:

$$ERDT_n = 0.5(\text{Artifact} + ((1 - RMI)ER_{Filter(n)}))$$

where the RMI is updated at predetermined intervals, with 21 hours being preferred (see block 322). Without limitation, the pacing output may then be updated according to a known suitable pacing protocol (see block 324). The next pace in the pacing step down protocol may be delivered (see loop 326). If after a pacing stimulus is delivered and the maximum amplitude of the electrocardiogram signal does not exceed the ERDT then a backup pace is delivered (see block 328). The artifact amplitude is then measured from the electrocardiogram signal (see block 330) and it is determined whether the autothreshold protocol is complete. If the protocol is not complete, the pacing output is updated according to known suitable pacing protocol (see loop 334, block 324 and loop 326). In this manner the detection threshold is defined greater than the amplitude for maximum artifact and less than the amplitude of the minimum evoked response.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A cardiac rhythm management device having a capture verification sensing circuit for use in at least one of a normal beat to beat stimulation mode and autothreshold mode, said cardiac rhythm management device including:
   (a) control means for selectively delivering electrical stimuli to a patient's heart and for detecting at least one of intrinsic and paced stimulations;
   (b) electrodes adapted to be positioned within the heart connected to an electrical conducting means for electrically connecting said electrodes to said control means; and
   (c) sensing means for sensing electrical activity of the patient's heart, said sensing means having a preamplifier electrically connected to said electrical conducting means, a first high pass coupling capacitor connected to said electrical conducting means between said electrode and said pre-amplifier, a blanking switch connected to said electrical conducting means between said high pass coupling capacitor and said pre-amplifier a high pass termination resistor connected to said electrical conducting means between said blanking switch and said pre-amplifier, a low pass coupling capacitor connected to said electrical conducting means between said blanking switch and said pre-amplifier a low pass resistor connected to said electrical conducting means between said blanking switch and said pre-amplifier and a low pass bi-pass switch connected to said electrical conducting means between said blanking switch and said pre-amplifier, said low pass bi-pass switch selectively connecting said low pass coupling capacitor and said low. pass resistor to said electrical conducting means, said sensing means including a dedicated evoked response amplifier.

2. The cardiac rhythm management device as recited in claim 1, further including a second sensing means for sensing electrical activity of the patient heart connected in parallel with said sensing means to said electrical conducting means, thereby creating a differential network to offset imbalance sensed from the electrode due to extraneous factors.

3. The cardiac rhythm management device as recited in claim 2, wherein said second sensing means has a second high pass coupling capacitor connected to said electrical conducting means between said electrode and said pre-amplifier, and a second blanking switch connected to said electrical conducting means between said second high pass coupling capacitor and said pre-amplifier, a second high pass termination resistor connected to said electrical conducting means between said second blanking switch and said pre-amplifier, a second low pass coupling capacitor connected to said electrical conducting means between said second blanking switch and said pre-amplifier, a second low pass resistor connected to said electrical conducting means between said second blanking switch and said pre-amplifier, and further including a second low pass bi-pass switch connected to said electrical conducting means between said second blanking switch and said pre-amplifier, said second low pass bi-pass switch selectively connecting said second low pass coupling capacitor and said second low pass resistor to said electrical conducting means.

4. The cardiac rhythm management device as recited in claim 3, further including a second input blanking means connected to said electrical conducting means between said second blanking switch and said pre-amplifier for selectively blanking sensed electrical activity.

5. A cardiac pacer having a capture verification sensing circuit for use in at least one of a normal beat to beat switch and said pre-amplifier, wherein each of said first and second sensing means has a low pass resistor coupled to said electrical conducting means between said blanking switch and said pre-amplifier, wherein each of said first and second sensing means has a low pass bi-pass switch coupled to said electrical conducting means between said blanking switch and said pre-amplifier, each said low pass bi-pass switch selectively coupling each said low pass coupling capacitor and each said low pass resistor to said electrical conducting means, and further including a dedicated evoked response amplifier coupled thereto.

* * * * *

UNITED STATES PATENT AND TRADEMARK OFFICE
CERTIFICATE OF CORRECTION

PATENT NO. : 6,427,085 B1 Page 1 of 1
DATED : July 30, 2002
INVENTOR(S) : Scot C. Boon, Mark Gryzwa, Michael Lyden, Qingsheng Zhu and Paul Haefner It is certified that error appears in the above-identified patent and that said Letters Patent is hereby corrected as shown below:

<u>Column 12,</u>
Line 21, after the second "beat", insert -- pacing mode and autothreshold mode, said cardiac pacer including:

(a) control means for selectively delivering electrical stimuli to a patient's heart and for detecting at least one of intrinsic and paced stimulations;

(b) electrodes adapted to be positioned within the heart coupled to an electrical conducting means for electrically coupling said electrodes to said control means;

(c) first and second sensing means electrically coupled in parallel to said electrical conducting means, said first and second sensing means for sensing electrical activity of the patient's heart and having a pre-amplifier electrically coupled to said electrical conducting means, each said first and second sensing means having a high pass coupling capacitor coupled to said electrical conducting means between said electrode and said pre-amplifier, and a blanking switch coupled to said electrical conducting means between said high pass coupling capacitor and said pre-amplifier, wherein each of said first and second sensing means has a high pass termination resitor coupled to said electrical conducting means between said blanking switch and said pre-amplifier, wherein each of said first and second sensing means has a low pass coupling capacitor coupled to said electrical conducting means between said blanking --

Signed and Sealed this

Seventeenth Day of December, 2002

JAMES E. ROGAN
*Director of the United States Patent and Trademark Office*